United States Patent [19]

Mayer et al.

[11] Patent Number: 5,084,567
[45] Date of Patent: Jan. 28, 1992

[54] SUBSTITUTED TETRACHALCOGENOFULVALENES AND A PROCESS FOR THEIR PREPARATION

[75] Inventors: Carl W. Mayer, Riehen; John Zambounis, Basel, both of Switzerland

[73] Assignee: Ciba-Geigy Corporation, Ardsley, N.Y.

[21] Appl. No.: 549,525

[22] Filed: Jul. 6, 1990

[30] Foreign Application Priority Data

Jul. 10, 1989 [CH] Switzerland .................. 2555/89

[51] Int. Cl.$^5$ .................. C07D 409/04; C07D 421/02
[52] U.S. Cl. .......................... 540/1; 549/15; 549/33; 549/37
[58] Field of Search .................. 540/1; 549/37, 40, 33, 549/15

[56] References Cited

U.S. PATENT DOCUMENTS 4,691,028  9/1987  Irokuchi .................. 549/36

Primary Examiner—Robert Gerstl
Attorney, Agent, or Firm—Kevin T. Mansfield

[57] ABSTRACT

Compounds of the formula I

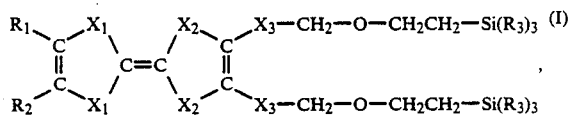

in which $X_1$, $X_2$ and $X_3$, independently of one another, are S or Se, $R_1$ and $R_2$, independently of one another, are H, linear or branched $C_1$–$C_{18}$alkyl-$X_4$- or $R_1$ and $R_2$ together are

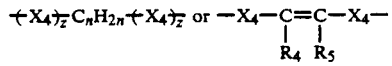

in which $X_4$ is S or Se, z is 0 and n is an integer from 2 to 6 or z is 1 and n is an integer from 1 to 4, $R_4$ and $R_5$, independently of one another, are H or $C_1$–$C_6$alkyl, and $R_3$ is linear or branched $C_1$–$C_{12}$alkyl or phenyl.

The compounds can be converted into unsymmetrically substituted chalcogenofulvalenes, from which electrically conducting charge-transfer complex salts can be prepared.

8 Claims, No Drawings

SUBSTITUTED TETRACHALCOGENOFULVALENES AND A PROCESS FOR THEIR PREPARATION

The invention relates to tetrachalcogenofulvalenes containing S or Se as heteroatoms and containing protective groups and a process for their preparation by coupling various vinylene trichalcogenocarbonates under the influence of trialkyl phosphites.

It is known that tetrachalcogenofulvalenes are $\pi$-donors for the preparation of charge-transfer complex salts, which have metallic properties. Of these, tetrachalcogenofulvalenes which are substituted unsymmetrically with respect to the double bond are also of interest, although their synthesis is difficult [N. C. Conella et al., J. Org. Chem. Vol. 43, p. 369–370 (1978)].

In Annals N.Y. Academy of Science, p. 355–360 (1978), M. P. Cava et al. describe the coupling of vinylene trithio- or vinylene dithioselenocarbonates substituted by methoxycarbonyl with benzotrithio- or benzodithioselenocarbonates under the influence of triethyl phosphite. The desired unsymmetrical tetrathiafulvalenes are only obtained in low yields and the proportion of the two other possible coupled products is only small when the selones, which are difficult to prepare, are used as starting materials.

It is desirable to provide heterofulvalenes which are obtainable in high yields and high purity and can be selectively converted into other unsymmetrical tetrachalcogenofulvalenes.

The invention relates to compounds of the formula I

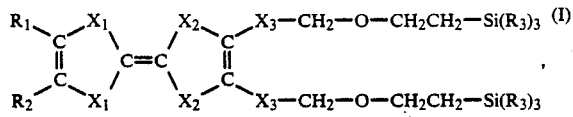

in which $X_1$, $X_2$ and $X_3$, independently of one another, are S or Se, $R_1$ and $R_2$, independently of one another, are H, linear or branched $C_1$-$C_{18}$alkyl or $C_1$-$C_{18}$alkyl-$X_4$- or $R_1$ and $R_2$ together are

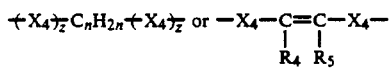

in which $X_4$ is S or Se, z is 0 and n is an integer from 2 to 6 or z is 1 and n is an integer from 1 to 4, $R_4$ and $R_5$, independently of one another, are H or $C_1$-$C_6$alkyl, and $R_3$ is linear or branched $C_1$-$C_{12}$alkyl or phenyl.

Each of the two $X_1$, $X_2$ or $X_3$ are preferably S or Se. Both $X_4$ are preferably each S or Se.

$R_1$ and $R_2$ as alkyl preferably contain 1 to 18, in particular 1 to 12, and especially 1 to 8, C atoms. Examples of alkyl are methyl, ethyl and the isomers of propyl, butyl, pentyl, hexyl, heptyl, octyl, nonyl, decyl, undecyl, dodecyl, tridecyl, tetradecyl, pentadecyl, hexadecyl, heptadecyl and octadecyl. $R_1$ and $R_2$ are particularly preferably H, methyl or ethyl.

$R_1$ and $R_2$ as alkyl-$X_4$- preferably contain 1 to 18, in particular 1 to 12, and especially 1 to 8, C atoms. Examples of alkyl have been mentioned above for $R_1$ and $R_2$. In the group alkyl-$X_4$-, examples of alkyl are particularly preferably methyl, ethyl, n-propyl, n-butyl, n-octyl, n-dodecyl and n-octadecyl.

$R_1$ and $R_2$ together can be the group $-(X_4)_z-C_nH_{2n}-(X_4)_z-$. Each of the $X_4$ is preferably S or Se. If z is 1, 0, n is preferably a number from 3 to 5. The group $-C_nH_{2n}-$ is a linear or branched alkylene group, which can be, for example, methylene, ethylidene, 1,2-ethylene, 1,1-, 2,2-, 1,2- or 1,3-propylene, 1,1-, 2,2-, 1,2-, 2,3-, 1,3- or 1,4-butylene, 1,1-, 2,2-, 3,3-, 1,2-, 1,3-, 1,4-, 3,4-, 2,4-, 2,5-pentylene, 1,1-, 2,2-, 3,3-, 1,2-, 1,3-, 1,4-, 1,5-, 1,6-, 2,3-, 2,4-, 2,5-, 2,6- and 3,4-hexylene.

If $R_1$ and $R_2$ together are the group

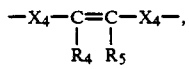

$R_4$ and $R_5$ are preferably H or $C_1$-$C_4$alkyl. Examples of alkyl are methyl, ethyl, n- or i-propyl, n-, i- or t-butyl, pentyl and hexyl. $R_4$ and $R_5$ are preferably H, methyl or ethyl.

Compounds of the formula I in which $R_1$ and $R_2$ are H, $C_1$-$C_{18}$alkyl or $C_1$-$C_{18}$alkyl-$X_4$-, z is 0 and n is a number from 3 to 5 or z is 1 and n is the number 1 or 2 constitute a preferred embodiment.

Another preferred embodiment is represented by those compounds of the formula I in which $R_1$ and $R_2$ are H or $C_1$-$C_{18}$alkyl, or $C_1$-$C_{18}$alkyl-S- or $C_1$-$C_{18}$-alkyl-Se-, or $R_1$ and $R_2$ together are $-(X_4)_z-C_nH_{2n}-(X_4)_z-$ in which $X_4$ is S or Se, z is 1 and the group $-C_nH_{2n}-$ is methylene, ethylene, 1,2-propylene, 1,3-propylene or 2,3-butylene, or z is 0 and the group $-C_nH_{2n}-$ is linear or branched $C_3$-$C_5$alkylene. If z is 0, the group $-C_nH_{2n}-$ is preferably 1,3-propylene or 1,4-butylene.

$R_3$ as alkyl preferably contains 1 to 6, in particular 1 to 4, C atoms. Examples of alkyl include methyl, ethyl, n- or i-propyl, n-, i- or t-butyl, and the isomers of pentyl, hexyl, heptyl, octyl, nonyl, decyl, undecyl or dodecyl. The group -Si($R_3$)$_3$ can contain identical or different alkyl radicals. $R_3$ is especially methyl.

The compounds of the formula I are obtainable in very pure form and are valuable intermediates for the preparation of unsymmetrical tetrachalcogenofulvalenes, which, as is known, are $\pi$-donors for charge-transfer complex salts. The silylethoxymethyl protective group can be selectively and stepwise substituted by reaction with N-substituted ammonium fluorides, for example tetrabutylammonium fluoride, in the presence of or with subsequent addition of alkyl or aralkyl halides or alkylene dihalides, in particular bromides or iodides, by alkyl, aralkyl and alkylene. This process has been described by V. Y. Lee in Synthetic Metals, 20 (1987), p. 161–167.

Charge-transfer complex salts are obtainable in a manner known per se by electrochemical oxidation of tetrachalcogenofulvalenes in an electrolyte solution containing conducting salts (see, for example, DE-A 3,504,144). These complex salts are organic electric conductors, which can be used, for example, for the preparation of electroactive materials or electrodes.

The invention also relates to a process for the preparation of compounds of the formula I according to claim 1, wherein a compound of the formula II

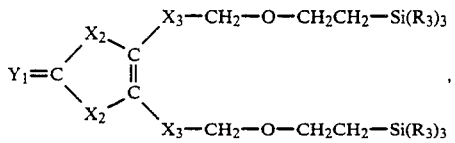

in which $Y_1$ is O, S or Se, and $X_2$, $X_3$ and $R_3$ are as defined above is reacted in the presence of a trialkyl phosphite with a compound of the formula III

in which $Y_2$ is O, S or Se, and $X_1$, $R_1$ and $R_2$ are as defined above.

$Y_1$ is preferably O or S.

The trialkyl phosphite is advantageously used in an amount of at least 2 moles per mole of the compound of the formula II. It is advantageous to use an excess to such an extent that the trialkyl phosphite can simultaneously serve as solvent.

The trialkyl phosphite can contain 3 to 36 C atoms and identical or different alkyl groups. It is preferred to use trialkyl phosphites of the formula $(C_1-C_6\text{-AlkylO})_3$P. Examples of alkyl groups have been mentioned under $R_1$. Examples of trialkyl phosphites are trimethyl, triethyl, tri-n-propyl, tri-n-butyl, methyldiethyl, dimethylethyl, n-propyldimethyl and n-butyldimethyl phosphite. Trimethyl and triethyl phosphite are particularly preferred.

The process can also be carried out in the presence of inert solvents, for example hydrocarbons, such as pentane, hexane, cyclohexane, methylcyclohexane, benzene, toluene and xylene, or ethers, such as diethyl ether, di-n-butyl ether, ethylene glycol dimethyl ether, ethylene glycol diethyl ether, diethylene glycol dimethyl ether, tetrahydrofuran and dioxane.

The reaction temperature can be, for example, 0° to 200° C., preferably 20° to 150° C.

The compounds of the formula III are generally known.

The compounds of the formula II can be prepared by a process described by G. Steinecke et al., Phosphorus and Sulfur, vol. 7, p. 49–55 (1979) by reacting a zinc compound of the formula IV

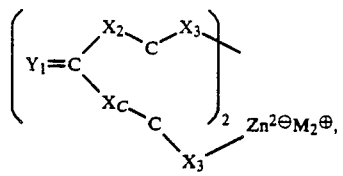

in which $Y_1$, $X_2$ and $X_3$ are as defined above and M is, for example, tetraalkylammonium with a protective group reagent of the formula

$(R_3)_3\text{Si-CH}_2\text{CH}_2\text{-O-CH}_2\text{-Cl}$.

The preparation of the zinc compounds of the formula IV is also described there. The 4,5-bis(benzoylthio)-1,3-dithiole-2-thione described there can be converted to the corresponding 4,5-bis(benzoylthio)-1,3-dithiol-2-one with mercury(II) acetate. The preparation of the protective group reagent has been described by B. H. Lipshutz et al. in Tetrahedron Letters, vo. 21, p. 3343–3346 (1980).

The compounds of the formulae II and III are used at least in equimolar amounts. It is advantageous to use an excess of the compounds of the formula II. The molar ratio of the compound of the formula II to the compound of the formula III can be, for example, 10:1 to 1:1, preferably 5:1 to 1:1.

The compounds of the formula I are obtained in surprisingly high yields, even if an excess of the compounds of the formula II is used. The symmetrical coupled products derived from the compounds of the formula II and from the compounds of the formula III are present in the reaction mixture merely in a surprisingly low proportion. The yields of the unsymmetrical compounds are more than 50% of theory and can be up to 90%. The SEM protective groups which are sensitive to basic reagents, for example fluoride ions, are not degraded by the basic trialkyl phosphites, in contrast to other known S- or Se-protective groups.

The compounds of the formula I can be isolated from the reaction mixture in high purity, which is of great significance for the reproducibility of the electrical properties of the charge-transfer complex salts of the unsymmetrical tetrachalcogenofulvalenes.

The isolation is preferably carried out by means of adsorption chromatography, which makes it possible to achieve very good separation in a simple manner without any major losses in yield. It is preferred to use silica gels as stationary phase. Preferably, nonpolar aprotic solvents or solvent mixtures are used as mobile phase. Examples are aliphatic, cycloaliphatic and aromatic hydrocarbons, for example pentane, hexane, octane, cyclopentane, cyclohexane, methylcyclohexane, benzene, toluene and xylene.

The invention also relates to compounds of the formula II

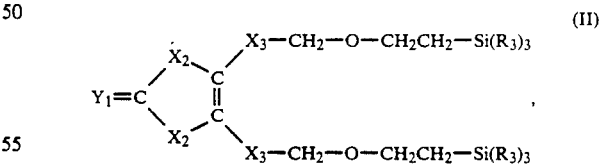

in which $Y_1$ is O, S or Se, $X_2$ is S or Se, $X_3$ is S or Se, and $R_3$ is linear or branched $C_1-C_{12}$alkyl or phenyl.

$X_2$, $X_3$ and $R_3$ have the preferred meanings mentioned for the compounds of the formula I. Those compounds of the formula II in which both $X_2$ or $X_3$ are each S or Se and $R_3$ is methyl are particularly preferred.

The examples which follow illustrate the invention in more detail. The temperature is given in degrees centigrade, unless stated otherwise. SEM is trimethylsilylethoxymethyl. THF is tetrahydrofuran.

(A)

PREPARATION OF STARTING MATERIALS

EXAMPLE A1

Preparation of

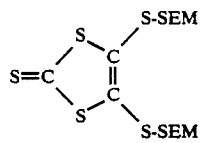

A solution of 7.1 ml (40 mmol) of 2-(trimethylsilyl)ethoxymethyl chloride [=SEM chloride] in 10 ml of tetrahydrofuran is added under argon over a period of 10 minutes to a saturated solution of 9.42 g (10 mmol) of [tetrabutylammonium]$_2$[(4,5-dithioisotrithione)$_2$Zn] in dry tetrahydrofuran. The deep purple solution turns yellow, and ZnCl$_2$ precipitates. The solvent is then removed in a water pump vacuum, and the residue is chromatographed on a silica gel column (50 cm long, 4 cm in diameter, 250 g of SiO$_2$) by means of methylene chloride. The first bright yellow band contains the desired compound. The yield is virtually quantitative (9 g, yellow-orange oil). NMR (CDCl$_3$), ppm$_{TMS}$: 0.05 (9H, -Si(CH$_3$)$_3$), 0.95–1.01 (2H, t), 3.65–3.75 (2H, t), 4.88 (2H, s).

EXAMPLE A2

Preparation of

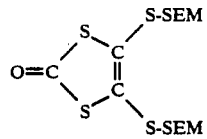

2.5 g (6.16 mmol) of bisbenzoyl-dithio-isotrithione are dissolved in a mixture of 100 ml of methylene chloride and 100 ml of glacial acetic acid at room temperature. 3.18 g (10 mmol) of mercury(II) acetate are added all at once, and the mixture is vigorously stirred for one hour. The colour of the solution turns from yellow-orange to colourless. At the same time, a white precipitate is formed. The reaction mixture is filtered through a G4 suction filter, the precipitate is washed with 100 ml of methylene chloride, and the filtrate is extracted three times with 200 ml of water. The organic phase is dried over magnesium sulfate and evaporated in a water pump vacuum. The bis(benzoyldithio)-isodithio-2-one (2.16 g, 89%) forms white needles of melting point 112° C.

1.95 g (5 mmol) of this intermediate are suspended under argon in 25 ml of methanol, and a solution of sodium methoxide [0.23 g (10 mmol) of Na in 4.6 ml of methanol] is added dropwise to this suspension over a period of 20 minutes. After the addition is completed, the orange solution is stirred for another 20 minutes, and a solution of 0.34 g of ZnCl$_2$ in 2.5 ml of methanol and 2.5 ml of 25% aqueous ammonia is then added dropwise. A concentrated solution of tetraphenylphosphonium bromide is added to the resulting dark orange solution with stirring, which precipitates the phosphonium complex

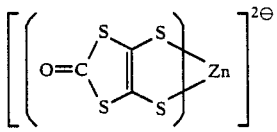

[Ph$_4$P$\oplus$]$_2$ in the form of a yellow solid. After 15 minutes, the product is filtered off with suction, washed with methanol, water, isopropanol and finally with ether. 2.67 g (87%) of the product are isolated; recrystallization from acetone leaves yellow needles of melting point 234°–235° C.

The crude product is used for the further reaction: 2.2 g (1.9 mmol) thereof are dissolved in a minimum amount of methylene chloride; 1.41 ml (8 mmol) of 2-(trimethylsilyl)ethoxymethyl chloride, dissolved in 3 ml of methylene chloride, are added to this solution under an inert gas atmosphere. After stirring for 30 minutes, the solvent is removed under a vacuum, and the residue is chromatographed on silica gel (250 g) by means of dichloromethane. The colourless product is the first to leave the column. It is a viscous oil. NMR (CDCl$_3$) ppm$_{(TMS)}$: 0.05 (9H, (CH$_3$)$_3$Si-), 0.95–1.01 (2H, T), 3.65–3.75 (2H, t), 4.88 (2H, S).

EXAMPLE A3

Preparation of

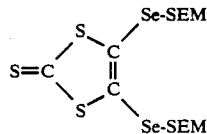

a) 10 g (0.074 mol) of vinylene trithiocarbonate, dissolved in 40 ml of dry tetrahydrofuran, are reacted with 0.15 mol of lithium isopropylamide [obtained from 21.1 ml (0.15 mol) of diisopropylamine, dissolved in 100 ml of dry tetrahydrofuran, and 100 ml (0.16 mol) of butyllithium (1.6M)] at −75° C. under argon to give the dilithiovinylene trithiocarbonate. 11.8 g (0.15 mol) of selenium are added to this yellow suspension also at −75° C. all at once, and the reaction mixture is allowed to thaw to room temperature overnight with constant stirring. After evaporation of the tetrahydrofuran,

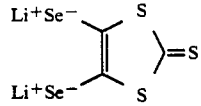

is obtained as an orange oil. It is dissolved in 160 ml of dry methanol. 8.85 g (0.065 mol) of zinc chloride, dissolved in 60 ml of methanol and 60 ml of 25% ammonia, are added dropwise over a period of 15 minutes, the mixture is stirred for 10 minutes, undissolved residues are filtered off, and 24 g (0.075 mol) of tetrabutylammonium bromide, dissolved in 30 ml of methanol, are added to this solution over a period of 15 minutes. A red powder precipitates, which is filtered off with suction, washed with a small amount of ice-cold methanol, isopropanol, water, again isopropanol and finally with diethyl ether to give 32.37 g (92% of theory) of the complex

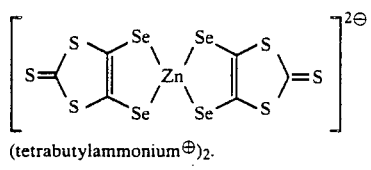

(tetrabutylammonium⊕)₂.

b) The title compound is obtained according to Example A1 by reaction of this complex with SEM chloride.

EXAMPLE A4

Preparation of

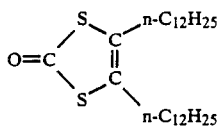

a) Acyloin condensation of methyl tridecanoate to give

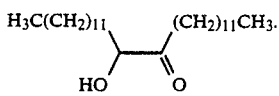

This compound is prepared analogously to the process described by V. L. Hansley in J.A.C.S. 57, 2303, (1935). After workup, the crude product (16 g, 81% of theory on a scale of 0.05 mol based on the product) is additionally recrystallized first from hot ethanol (40 ml), and the compound (10.6 g) which precipitates at room temperature is chromatographed on a column (8 cm in diameter and 50 cm in length) over silica gel first with dichloromethane and then with diethyl ether. The pure product (10.2 g of white needles) has a melting point of 66°–69° C.

b) Chlorination of the acyloin to give

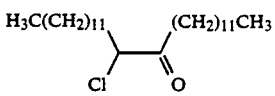

A solution of 10 g (0.025 mol) of the acyloin from a) and 2.95 ml (0.037 mol) of pyridine in 260 ml of dichloromethane is added dropwise over a period of 1 hour to an ice-cold solution of 2.35 ml (0.031 mol) of thionyl chloride and 0.75 ml (0.009 mol) of pyridine in 35 ml of dichloromethane. The solution is stirred at room temperature overnight and then cooled with 100 ml of ice water. The organic phase is washed three times with 100 ml each of water, dried with Na₂SO₄ and evaporated in vacuo. The oily crude product is chromatographed on a column (8 cm in diameter, 50 cm in length) over silica gel and by means of dichloromethane:hexane (1:2) as mobile phase. The first fraction consists of the pure product, 7.3 g (about 70% of theory); white crystals of melting point 42°–44° C.

c) Preparation of

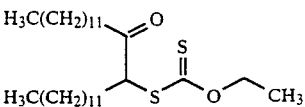

A suspension of 7 g (0.017 mol) of the α-chloroketone from b) and 2.71 g (0.017 mol) of potassium ethylxanthogenate in 150 ml of acetone are stirred overnight at room temperature in the absence of moisture. The reaction mixture is filtered and 2 l of water are then added to the filtrate. The oil which separates is extracted with 400 ml of diethyl ether, the solution is dried and evaporated. 8 g (about 95% of theory) of a light yellow oil remain, which is purified on a small flash chromatography column (4 cm in diameter; 25 cm in length) by means of dichloromethane. MS FD: M⁺ = 500.

d) Preparation of

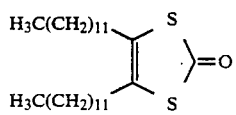

7.9 g of the xanthogenate from c) are stirred in 40 ml of 30% hydrogen bromide in acetic acid at room temperature for 2 hours. 300 ml of water are then added, and the oil which separates is extracted three times with 100 ml each of diethyl ether. The organic phase is washed three times with 200 ml each of water, dried and evaporated. The resulting oil is further dried in a high vacuum: 6.8 g (about 93% of theory) of a slightly yellow oil. MS: M⁺ = 454 (100%).

EXAMPLE A5

Preparation of

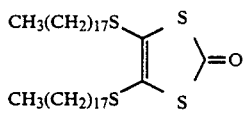

2.7 g (0.0029 mol) of the zinc complex according to Example A1 are dissolved in 140 ml of acetone, and 5.7 g (about 0.0043 mol) of 1-bromooctadecane are added. The solution is stirred at room temperature for 4 days, and the precipitated citrus yellow solid is filtered off and repeatedly washed with water and acetone. Yield 4 g (about 100% of theory); melting point 78° C. The thioketone obtained is converted to the ketone with mercury acetate analogously to Example A2: yield 72%. White crystals, melting point 71°–72° C.

EXAMPLE A6

Preparation of

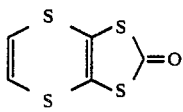

The compound is prepared by the process described by K. S. Varma et al. in Physica 143B, p. 321 (1986). Melting point 123°–125° C.

(B)

PREPARATION OF SEM-PROTECTED TETRACHALCOGENOFULVALENES

EXAMPLE B1

Preparation of

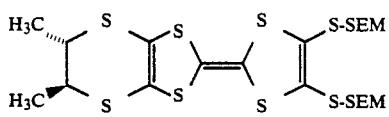

780 mg (3.3 mmol) of

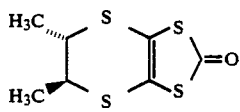

[see Helvetica Chimica Acta, Vol. 69, p. 69–70 (1986)] and 3.03 g (6.6 mmol) of the compound according to Example A1 are dissolved under argon in 17 ml of freshly distilled triethyl phosphite, and the solution is heated at 105° C. for 3.5 hours with stirring. After the solution has cooled to room temperature, the triethyl phosphite is evaporated off in a high vacuum. The oily residue thus obtained is eluted over silica gel by means of benzen:hexane (2:1). The orange frontal zone gives 52 mg of tetramethylbis(ethylenedithio)tetrathiafulvalene, the middle red zone 1.9 g (89%) of the desired product in the form of an oil and the last brick red zone 700 mg of tetra-S-SEM-tetrathiafulvalene (orange needles). UV (CH₃CN) nm: 470, 375(sh), 337(sh), 312, 299(sh), 250(sh), 229; MS (m/e): 646 (M+, 11%), 73 ((CH₃)₃Si-, 100%).

EXAMPLE B2

Preparation of

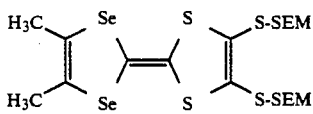

450 mg (1.4 mmol) of dimethylvinylene triselenocarbonate [K. Bechgaard et al., J. Org. Chem., 1983, (48), 388–389] and 1.92 g (4.2 mmol) of the compound according to Example A1 are dissolved in 10 ml of freshly distilled triethyl phosphite and stirred under argon at 105° C. for 3.5 hours. After cooling, the excess triethyl phosphite is removed in a high vacuum. The resulting dark red viscous oil is chromatographed over silica gel (500 g) by means of a benzene:hexane mixture (2:1). The first violet band gives 20 mg (6%) of tetramethyltetraselenofulvalene. The next red band contains 380 mg (37%) of the desired compound, which is a brick red oil affording brick red small needles of melting point 68°–69° C. after a few days.

EXAMPLES B3 TO B11

The procedure of Example B1 is repeated. The molar ratio of the compounds A to B (see Table 1) is 1:2 (in Examples B5 and B8–B10 1:1). In Examples B7 and B11, benzene is used as solvent. The theoretic ratio of the compounds AB:AA:BB in the reaction mixture is 50:20:30 (50:25:25 in Examples B5 and B8–B10). The results are summarized in Table 1 below.

TABLE 1

| | Compound A | Compound B | Ratio AB:AA:BB (experimental) |
|---|---|---|---|
| B1 | CH₃ substituted dithiole with =O | SEM-protected dithiole | 78:2:20 |
| B2 | H₃C-substituted diselenole with =Se | SEM-protected dithiole | 15:1:* |
| B3 | ethylenedithio dithiole with =O | SEM-protected dithiole | 79:2:19 |
| B4 | dithiolene with =O | SEM-protected dithiole | 76:2:22 |
| B5 | dithiolene with =O | SEM-protected dithiole | 95:1:4 |

TABLE 1-continued

| | Compound A | Compound B | Ratio AB:AA:BB (experimental) |
|---|---|---|---|
| B6 | CH₃ substituted dithiole-dithiole with =O | SEM-protected vinyl dithiolate with S= | 77:2:21 |
| B7 | (H₃C)₂C= dithiole with =S | SEM-protected vinyl dithiolate with O= | 15:1:* |
| B8 | ethylenedithio dithiole with =O | SEM-protected vinyl dithiolate with S= | 91:4:5 |
| B9 | propylenedithio dithiole with =O | SEM-protected vinyl dithiolate with S= | 86:4:10 |
| B10 | (CH₃(CH₂)₁₇S)₂C= dithiole with =O | SEM-protected vinyl dithiolate with S= | 71:19:10 |
| B11 | (H₃C(CH₂)₁₁)₂C= dithiole with =O | SEM-protected vinyl dithiolate with S= | 18:0:82 |

*not isolated

(C) PREPARATION OF UNSYMMETRICAL TETRACHALCOGENOFULVALENES

EXAMPLE C1

Preparation of

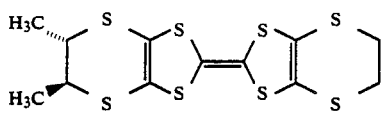

244 mg (0.38 mmol) of the compound of Example B1 are dissolved in 27 ml of dry tetrahydrofuran. 0.16 ml (1.9 mmol) of 1,2-dibromomethane and 1.7 ml of tetrabutylammonium fluoride solution in THF (1.0M solution) are added dropwise under argon. After stirring at room temperature for four days, the solvent is evaporated on a rotary evaporator, and the residue is chromatographed over a silica gel column. The eluent is a 2:1 mixture of benzene and hexane. The frontal zone affords 11 mg of the title compound in the form of orange crystals of melting point 203° C.

EXAMPLE C2

Preparation of

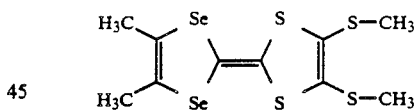

140 mg (0.21 mmol) of the compound according to Example B2 are dissolved in 2 ml of dry tetrahydrofuran under argon, and 5 ml of 1-molar tetrabutylammonium fluoride solution in THF are added. The colour of the reaction solution rapidly changes to dark red. After stirring for one hour, methyl iodide is slowly added dropwise until the colour has become light orange. An excess of metal iodide leads to the precipitation of tetrabutylammonium iodide and prevents the removal of the second SEM group. If such an excess is avoided, the solution again adopts a dark red colour (elimination of the second SEM group). After another 30 minutes, methyl iodide is again added dropwise until the colour has become light orange. After detecting on the thin-layer chromatogram (silica gel; benzene:hexane 1:1) only the one spot of desired product, the solvent is evaporated in a water pump vacuum, and the residue is chromatographed over silica gel (350 g). The eluent is methylene chloride. The orange-red band affords 85 mg (94%) of the desired product in the form of brick red crystals of melting point 100° C.

EXAMPLE C3

Preparation of

[structure: bicyclic compound with Se, Se (left ring) and S, S (center) and S, S (right ring)]

According to Example B2, vinyl triselenocarbonate and the compound according to Example A1 are reacted to give the compound

[structure: Se, Se ring with C=C linkage to C(S-SEM)(S-SEM)]

This compound is reacted according to Example C2 with 1,2-dibromomethane to give the title compound in the form of orange needles of melting point 208° C. (yield 30%).

EXAMPLE C4

Preparation of

[structure: dithiole-dithiole-C(SeCH3)(SeCH3)]

The reaction of the compound of Example B8 according to Example C2 affords the title compound.

EXAMPLE C5

Preparation of

[structure: vinyl-dithiole-dithiole-C(SCH3)(SCH3)]

The reaction of the compound of Example B9 according to C2 affords the title compound of melting point 117° C.

EXAMPLE C6

Preparation of

[structure: n-C18H37S, n-C18H37S—C=C(S,S)—C(S,S)=C(SCH3)(SCH3)]

The reaction of the compound of Example B10 according to Example C2 affords the title compound of melting point 72° C.

EXAMPLE C7

Preparation of

[structure: n-C12H25, n-C12H25—C=C(S,S)—C(S,S)=C(SCH3)(SCH3)]

The reaction of the compound of Example B11 according to Example C2 affords the title compound of melting point 65° C.

(D)

Preparation of charge-transfer complex salts

EXAMPLE D1

Preparation of $$\left[ \text{[Se,Se-ring-C=C(S,S)-C(S,S)-ring]} \right]_2^{\oplus} \quad IBr_2^{\ominus}$$

15 mg of the compound according to Example C3 are introduced into the anode space of an electrolysis cell of 30 ml in volume. 80 mg tetrabutylammonium $IBr_2$ as the conducting electrolyte are poured into the cell under argon. Dichloromethane is used as the solvent. The cell is allowed to stand for four hours, and then the current is adjusted to 0.5 μA (Pt wire electrodes 1×20 mm). After one week, the black platelets of the title compound can be isolated.

The electric conductivity of this complex is $\sigma_{RT} = 10^3$ ohm$^{-1}$ cm$^{-1}$. Upon cooling to 2K, it increases by a factor of about 12.5 during which no transition to a semi-conducting state is observed.

What is claimed is:

1. A compound of the formula I $$\begin{array}{c} R_1 \\ \diagdown \\ C \\ \| \\ C \\ \diagup \\ R_2 \end{array} \begin{array}{c} X_1 \\ \diagdown \\ \diagup \\ X_1 \end{array} C=C \begin{array}{c} X_2 \\ \diagdown \\ \diagup \\ X_2 \end{array} \begin{array}{c} \diagdown \\ C \\ \| \\ C \\ \diagup \end{array} \begin{array}{c} X_3-CH_2-O-CH_2CH_2-Si(R_3)_3 \\ \\ X_3-CH_2-O-CH_2CH_2-Si(R_3)_3 \end{array} \quad (I)$$

in which $X_1$, $X_2$ and $X_3$, independently of one another, are S or Se, $R_1$ and $R_2$, independently of one another, are H, linear or branched $C_1$-$C_{18}$alkyl or $C_1$-$C_{18}$alkyl-$X_4$- or $R_1$ and $R_2$ together are $$-\!\!\left(X_4\right)_{\overline{z}} C_n H_{2n} \!\!\left(X_4\right)_{\overline{z}}\!\!- \text{ or } -X_4-\underset{\underset{R_4}{|}}{C}=\underset{\underset{R_5}{|}}{C}-X_4-$$

in which $X_4$ is S or Se, z is 0 and n is an integer from 2 to 6 or z is 1 and n is an integer from 1 to 4, $R_4$ and $R_5$, independently of one another, are H or $C_1$-$C_6$alkyl, and $R_3$ is linear or branched $C_1$-$C_{12}$alkyl or phenyl.

2. A compound according to claim 1, in which both $X_1$, $X_2$ or $X_3$ are S or Se.

3. A compound according to claim 1, in which $R_1$ and $R_2$ are H, $C_1$-$C_{18}$alkyl or $C_1$-$C_{18}$alkyl-$X_4$-, z is 0 and n is a number from 3 to 5 or z is 1 and n represents the numbers 1, 2 or 3.

4. A compound according to claim 1, in which $R_4$ and $R_5$ are H, methyl or ethyl.

5. A compound according to claim 1, in which $R_3$ is $C_1$–$C_4$alkyl.

6. A compound according to claim 5, in which $R_3$ is methyl.

7. A compound according to claim 1, in which $R_1$ and $R_2$ are H or $C_1$–$C_{18}$alkyl or $C_1$–$C_{18}$alkyl-S- or $C_1$–$C_{18}$alkyl-Se-, or $R_1$ and $R_2$ together are $-(X_4)_z-C_nH_{2n}-(X_4)_z-$ in which $X_4$ is S or Se, z is 1 and the group $-C_nH_{2n}-$ is methylene, ethylene, 1,2-propylene, 1,3-propylene or 2,3-butylene, or z is 0 and the group $-C_nH_{2n}-$ is linear or branched $C_3$–$C_5$alkylene.

8. A compound according to claim 7, in which z is 0 and the group $-C_nH_{2n}-$ is 1,3-propylene or 1,4-butylene.

* * * * *